United States Patent [19]

Fischer

[11] 4,450,834
[45] May 29, 1984

[54] EXTERNAL FIXATION DEVICE

[75] Inventor: David A. Fischer, Minneapolis, Minn.

[73] Assignee: Ace Orthopedic Manufacturing, Inc., Los Angeles, Calif.

[21] Appl. No.: 290,740

[22] Filed: Aug. 7, 1981

Related U.S. Application Data

[62] Division of Ser. No. 85,996, Oct. 18, 1979, Pat. No. 4,308,863.

[51] Int. Cl.³ .............................................. A61F 5/04
[52] U.S. Cl. ............................ 128/92 EB; 128/92 A
[58] Field of Search ................ 128/92 EB, 92 A, 1 R, 128/92 D

[56] References Cited

U.S. PATENT DOCUMENTS

| 2,301,500 | 11/1942 | Anderson | 128/92 EB |
| 2,500,370 | 3/1950 | McKibbin | 128/92 EB |
| 2,725,053 | 11/1955 | Bambara et al. | 128/92 EB |
| 3,765,034 | 10/1973 | Johnston | 128/92 EB |
| 3,993,055 | 11/1976 | Volkov et al. | 128/92 A |
| 4,006,740 | 2/1977 | Volkov et al. | 128/92 A |
| 4,299,212 | 11/1981 | Goudfrooy | 128/92 EB |
| 4,349,017 | 9/1982 | Sayegh | 128/92 A |

FOREIGN PATENT DOCUMENTS

| 646558 | 8/1935 | Fed. Rep. of Germany | 128/92 EB |
| 168885 | 1/1951 | Fed. Rep. of Germany | 128/92 EB |
| 2830566 | 1/1980 | Fed. Rep. of Germany | 128/92 EB |
| 1448111 | 9/1976 | United Kingdom | 128/92 EB |

Primary Examiner—C. Fred Rosenbaum
Assistant Examiner—C. W. Shedd
Attorney, Agent, or Firm—Hubbard & Stetina

[57] ABSTRACT

An improved external fixation device is disclosed composed of a pair of arcuate frame segments and multiple adjustment rods and pin holders, which cooperate with one another as well as plural pins extending through the soft tissue and bone of a patient to rigidly immobilize a bone fracture and permit compression, neutralization or distraction of the fracture from a location external to the body.

5 Claims, 13 Drawing Figures

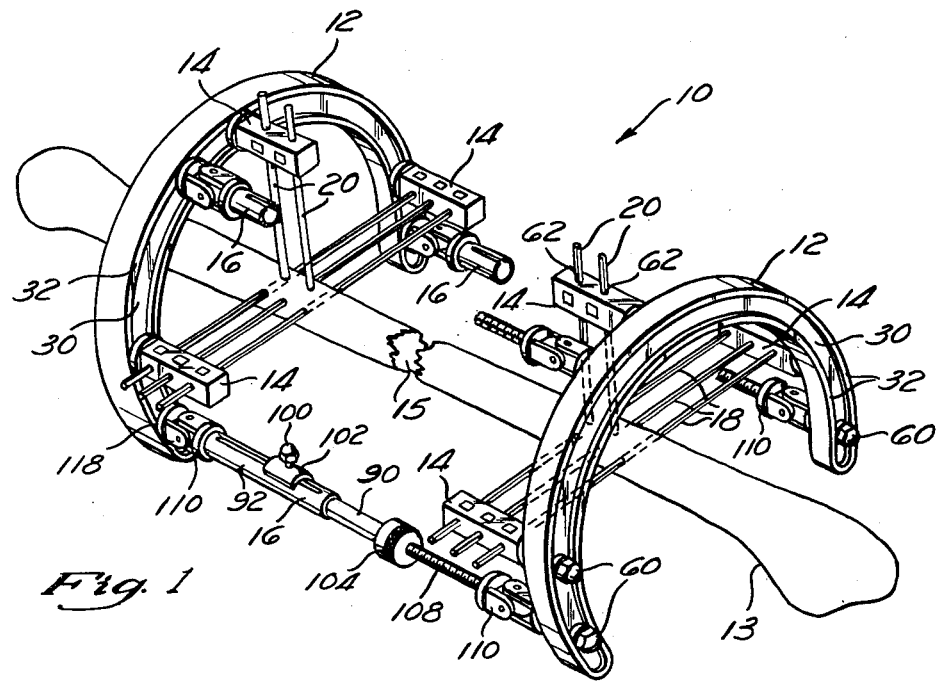
Fig. 1
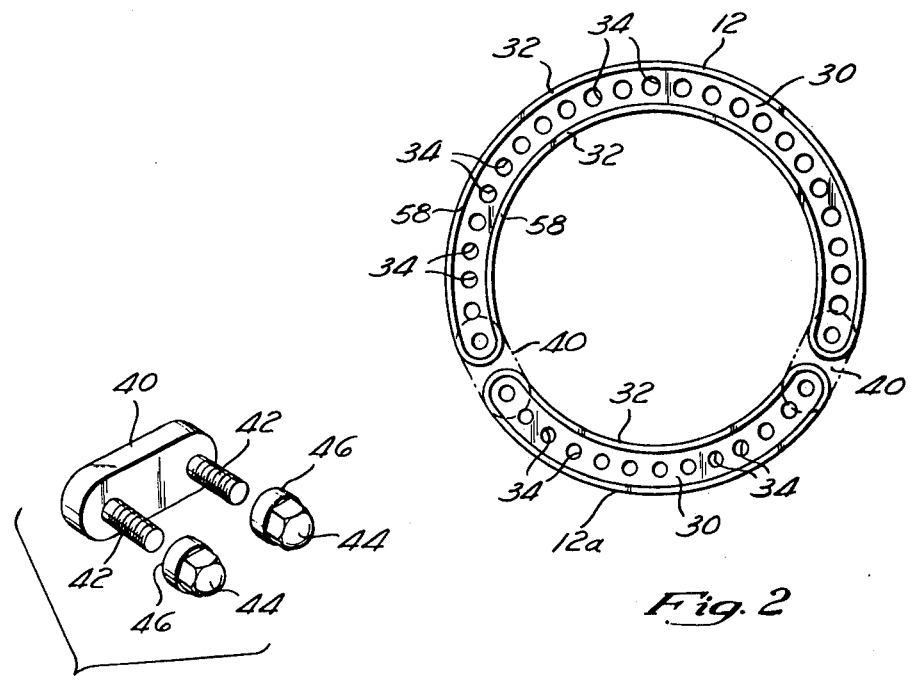
Fig. 2
Fig. 2A

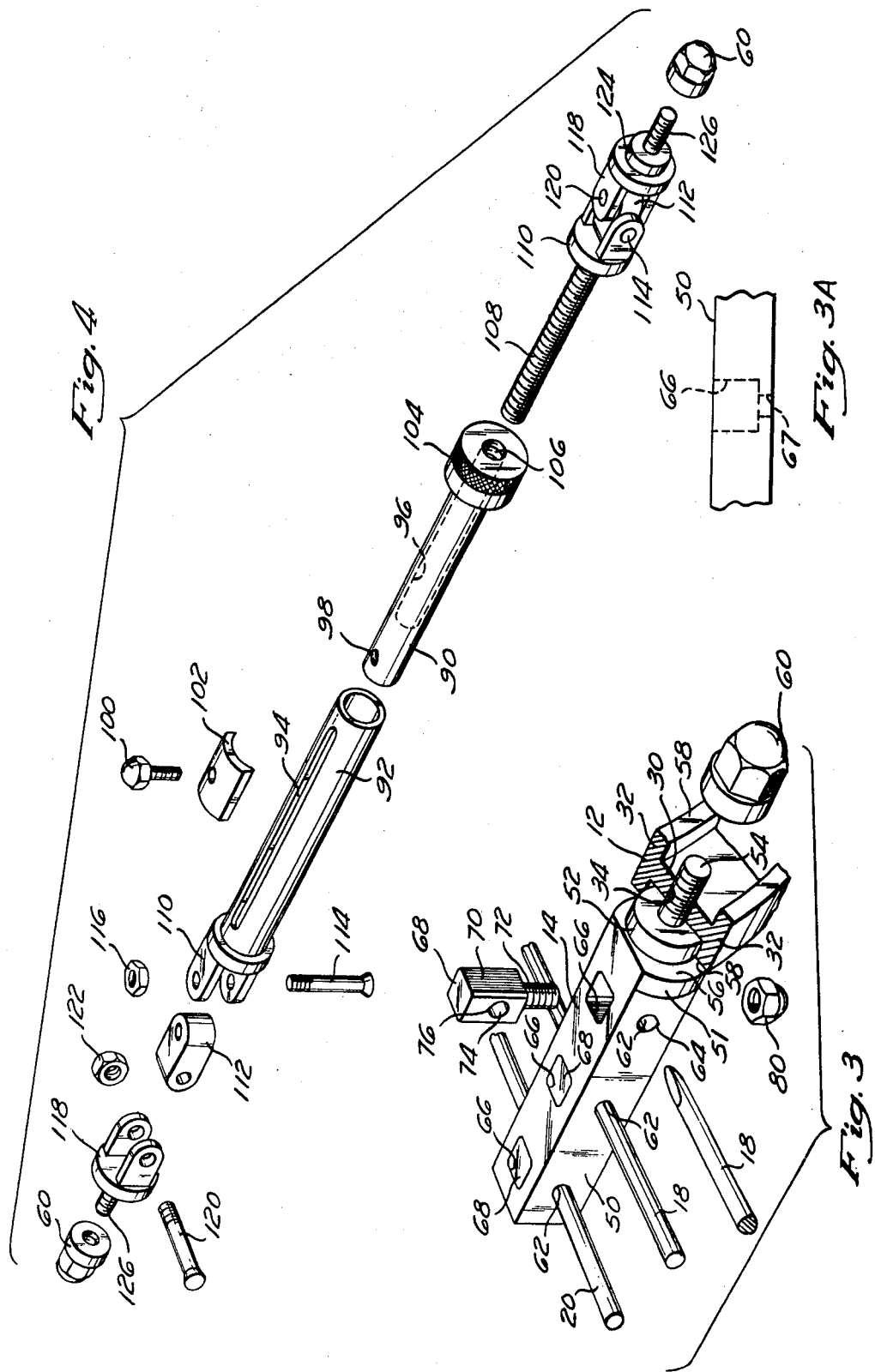

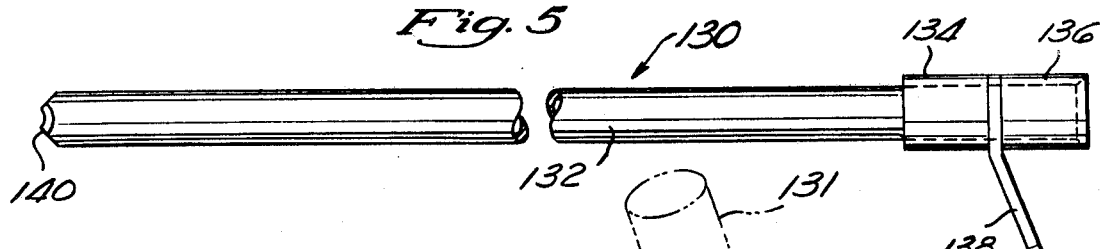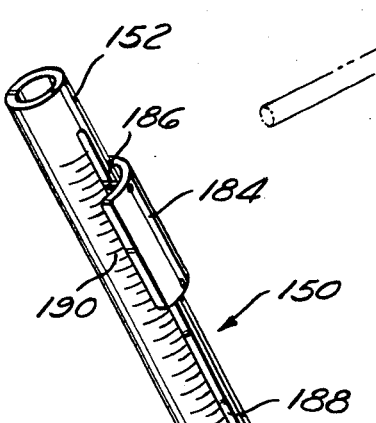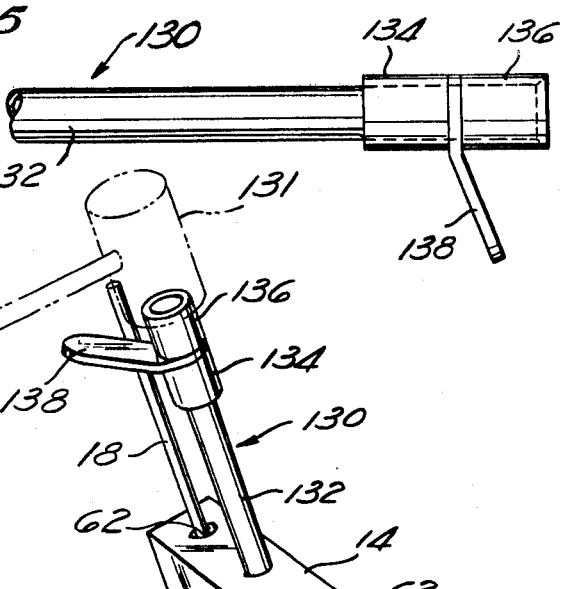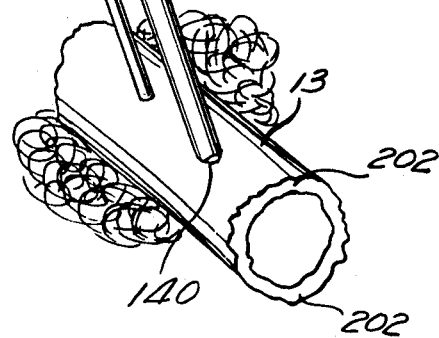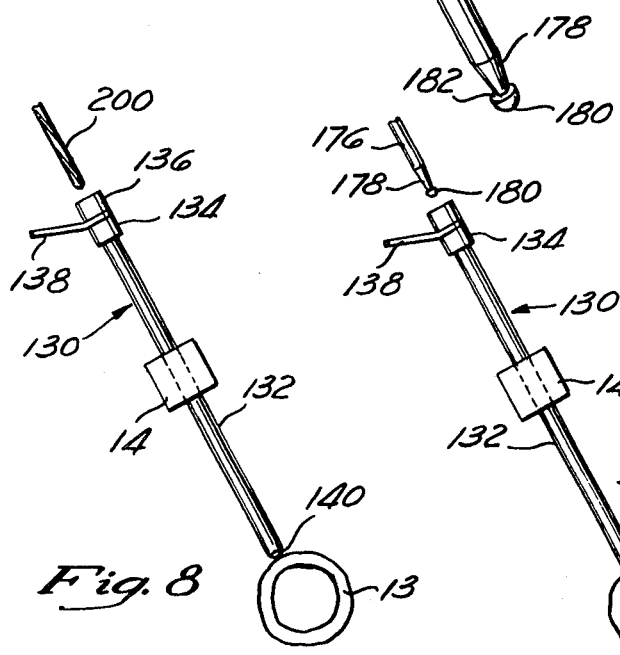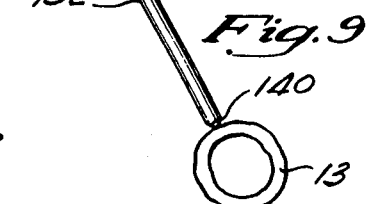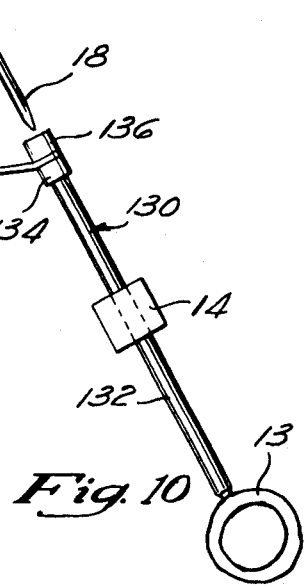

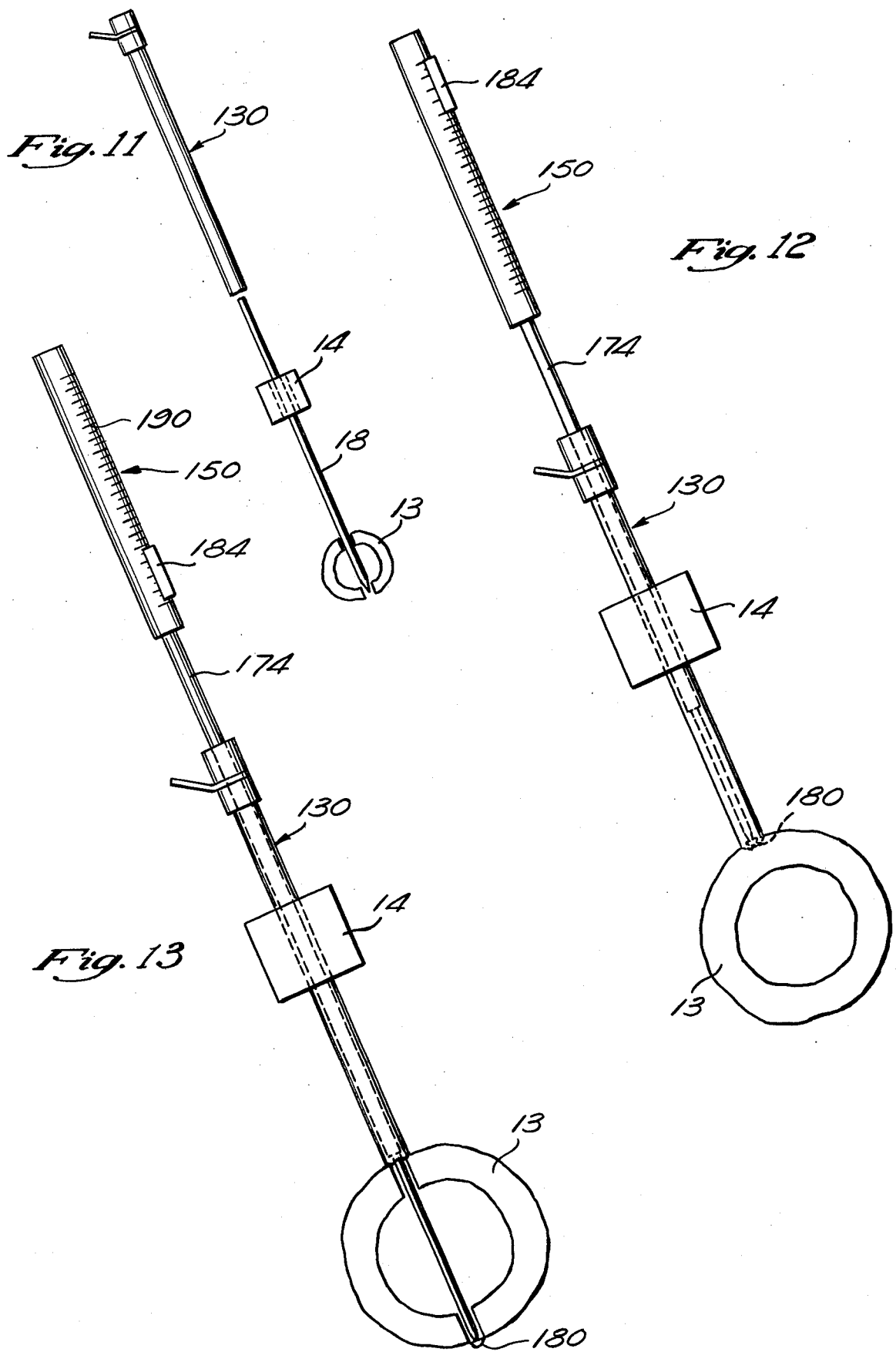

EXTERNAL FIXATION DEVICE

This application is a division of application Ser. No. 85,996, filed Oct. 18, 1979 now U.S. Pat. No. 4,308,863.

BACKGROUND OF THE PRESENT INVENTION

The present invention relates to orthopedic medical apparatus and more particularly to medical apparatus utilized to treat bone fractures wherein repositioning and immobilization of the fractured bone is facilitated by means external of the body soft tissue; such apparati are referred to very broadly as external fixation devices.

External fixation has long been recognized as a viable mean for treating fractures of the bones, with the first reasonably successful use of such external fixation devices being traced back to the early 20th century. Since its inception, there have been various external fixation systems developed, all of which in one form or another utilize a plurality of transfixing and/or half pins which extend through the bone and outward beyond the slot tissue surrounding the bone. The multiple pins are positioned on opposite sides of the fracture and rigidly attached to one or more pin couplings at their distal ends. The pin couplings are interconnected by a mounting bar which permits the bone portions located on opposite sides of the fracture to be repositioned relative one another and maintained in an aligned position which after a sufficient period of time, permits proper healing of the fracture. Although such prior art external fixation apparatus has proven useful in specific applications, there are inherent deficiencies associated in its general use.

Foremost of these deficiencies is the prior art's inability to provide sufficient rigidity to ensure complete immobilization of the bone fracture during the rehabilitation period. This lack of rigidity focuses upon the prior art's typical use of the transfixing pins themselves to form the major portion of the exterior load bearing structure of the device. Although the transfixing pins are typically fabricated from hardened stainless steel, due to their substantial length in relation to their cross-sectional area, they tend to moderately flex when subjected to tensile and bending forces. Such flexing permits the bone portions to move relative one another during movement of the patient's limb extremities, thereby varying the bone placement and detracting from the healing process.

Additionally, the prior art external fixation device has typically comprised rather large bulky mechanical apparatus which extends substantially outward beyond the soft tissue in the vicinity of the fracture. Such outward protrusion and bulkiness of the fixation structure not only results in discomfort to the patient but in the case of an open fracture, limits access to the soft tissue making necessary treatment of the soft tissue such as skin grafting or irrigation difficult.

Further, the prior art external fixation devices have heretofore facilitated only limited pin placement and have failed to provide any means for the independent removal or adjustment of individual pins on the apparatus without disturbing the remaining pins of the external fixation. As such, the prior art devices have often limited the orthopedic surgeon during operative installation of the device upon the patient as well as in postoperative adjustment and modifications.

Thus, there exists a substantial need for an external fixation device, which when mounted upon a patient provides sufficient rigidity to completely immobilize the bone fracture, provides relatively unlimited pin placement, and permits ready access to the fracture sight for soft tissue treatment.

SUMMARY OF THE PRESENT INVENTION

The present invention comprises an improved external fixation device, which significantly eliminates the deficiencies associated in the prior art. Specifically, the present invention comprises an external fixation device composed of three major components, an arcuate frame segment, an adjustment rod and pin holder, which when connected in combination with suitable pin members attached to the bone, yields a rigid external fixation system, capable of immobilizing the fracture and facilitating either compression, neutralization or distraction of the bone fracture.

The arcuate frame segments of the external fixation device of the present invention are formed having an I-beam cross-sectional configuration to yield maximum strength with minimum weight and are adapted to extend closely about the soft tissue in the vicinity of the fracture site. The pin holders as well as the adjustment rods are specifically fabricated to be mounted directly to the arcuate frame segments, at any location along the length thereof. The direct attachment of the pin holders and adjustment rods to the frame segments places the applied forces of the entire system on the frame segments, thereby reducing bending and tensile stresses exerted upon the pins and yields a substantially rigid external frame structure. Relative movement of the bone portions during rehabilitation is eliminated, thereby ensuring proper healing. In addition, the pin holders may be positioned at any location along the length of the frame segments. The orthopedic surgeon is, therefore, not limited by the apparatus as to proper pin placement and may install the device upon the patient in the manner most conducive for proper bone repositioning and immobilization.

Further, the present invention provides a unique pin holder construction which is capable of positively clamping single or multiple pin members and further permits individual pins to be adjusted or removed from the pin holder without disturbing the remaining pins on the device. The present invention thus permits readjustment of particular pin members during installation of the device, or alternatively removal of selected pins to permit improved healing during postoperative care.

Additionally, the adjustment rods of the present invention are specifically designed to augment the arcuate frame segments by providing full lateral and angular adjustment between the frame segments during installation and providing a rigid structure when locked into position by the surgeon. The adjustment rods are provided with full coarse and fine length adjustment means which facilitate rapid pre-alignment of the bone ends and subsequent distraction or compression of the fracture.

Further, the present invention discloses a novel sheath and a novel method which permits proper alignment, drilling and placement of the pins into the bone with only minimal damage to soft tissue, as well as a bone depth gauge which is insertable within the sheath to accurately measure the bone diameter thereby facilitating proper pin selection and insertion into the bone.

These as well as other features of the present invention will become more apparent upon reference to the drawings wherein:

FIG. 1 is a perspective view of the improved external fixation device of the present invention installed upon a fractured bone illustrating the relative orientation of the arcuate frame segments, pin holders, adjustment rods and pins with the bone;

FIG. 2 is a plan view of the two preferred angular lengths of the arcuate frame segments of the present invention oriented to be rigidly connected together;

FIG. 2A is a perspective view of a frame connector utilized to rigidly interconnect the two arcuate frame segments of FIG. 2;

FIG. 3 is a partially exploded perspective view of the pin holder of the present invention illustrating its detailed construction and showing its interconnection with the arcuate frame segment;

FIG. 3A is a side view of a portion of a pin holder showing the shape of the pocket therein;

FIG. 4 is an exploded perspective view of the adjustable connecting rod of the present invention;

FIG. 5 is a perspective view of the pin sheath of the present invention which is insertable into the pin holder of FIG. 3;

FIG. 6 is a perspective view of the sheath of FIG. 5 installed within the pin holder and extending downward through the soft tissue into the outer surface of the bone;

FIG. 7 is a perspective view of the bone depth gauge of the present invention;

FIG. 8 is a schematic view of the sheath of FIG. 5 being utilized as a drill guide;

FIG. 9 is a schematic view of the sheath of FIG. 5 being utilized in conjunction with the bone depth probe of FIG. 7 to accurately measure the diameter of the bone;

FIG. 10 is a schematic view of the sheath of FIG. 5 being utilized to guide the insertion of a pin into the bone;

FIG. 11 is a schematic view of the sheath of FIG. 5 being withdrawn to leave the pin inserted in the bone;

FIG. 12 is a schematic view of the sheath of FIG. 5 being used in conjunction with the depth probe of FIG. 7 to obtain an initial reading on the probe representing the position of the top surface of the bone; and FIG. 13 is a schematic view of the sheath of FIG. 5 being used in conjunction with the depth probe of FIG. 7 to obtain a final reading on the probe representing the position of the lower, outer surface of the bone for measuring the diameter of the bone.

FIGS. 6, 8, 9 and 10 to 13 together depict steps of the process of this invention.

DETAILED DESCRIPTION OF THE PREFERRED EMBODIMENT

FIG. 1 depicts the improved external fixation device 10 of the present invention composed generally of a pair of arcuate frame segments 12, which are disposed about a fractured bone 13 having plural pin holders 14 and multiple adjustment rods 16 attached thereto. As shown, the pin holders 14 are positioned at various locations upon the arcuate support segments 14, and mount plural transfixing pins 18 which extend completely through the fractured bone 13 and outward beyond the soft tissue (not shown) surrounding the bone 13 and plural half pins 20 which extend through the fractured bone 13 but protrude only a short distance beyond the lower surface thereof.

The transfixing pins 18 and half pins 20 are arranged upon the bone 13 to provide two independent pin groups which are disposed on opposite sides of the bone fracture 15 and rigidly attached by the pin holders 14 to a respective one of the arcuate frame segments 12. The relative lateral and angular position of the arcuate frame segments 12 is maintained by the plural adjustment rods 16 which are rigidly attached at opposite ends thereof to each of the arcuate frame segments 12. The specific orientation of the frame segments 12 about the fractured bone 13 as well as the number of pins 18 and 20 utilized, and their position upon the apparatus 10 as shown in FIG. 1, is merely disclosed as by way of example, with adaptations and modifications of the basic structure being contemplated to suit the particular fracture type and fracture location upon the patient.

Referring to FIG. 2, the detailed construction of the arcuate frame segments 12 of the present invention is illustrated. In the preferred embodiment, the frame segments 12 are typically fabricated in two angular lengths, 240° and 120°; designated by the numerals 12 and 12a respectively in FIG. 2, which may be utilized either singularly as shown in FIG. 1, or conjunctively as represented in FIG. 2 to yield the proper frame orientation to suit the particular type and location of bone fracture 15. Of course, the frame segments may be in various lengths. Both of the frame segments 12 and 12A are also provided in different diameter sizes to account for variations in the fracture location and body size of the patient with the various sizes being readily interchangeable to permit the proximal and distal frame members, located on opposite sides of the fracture to be of unequal diameter size.

The arcuate frame segments 12 and 12a are formed having an I-beam cross-section composed of a central web portion 30 and a pair of flange portions 32 (best shown in FIGS. 2 and 3) sized having standard cross-sectional dimensions for all of the various segment sizes. A plurality of mounting apertures 34 are formed in the web portion 30 and symmetrically spaced at approximately 8° intervals throughout the length of the frame segments 12 and 12a. In the preferred embodiment, the segments 12 and 12a are fabricated using powdered metallurgy production techniques to yield minimum weight and provide maximum strength, however, other standard machining processes using materials such as stainless steel and titanium are equally applicable.

In the particular instances which require an entire circular support frame to be disposed about the soft tissue of a patient, the arcuate frame segments 12 and 12a may be joined together by use of a connecting link 40 illustrated in FIG. 2A. As shown the connecting link 40 includes a pair of threaded studs 42 the diameter of which is sized slightly less than the diameter of the plural apertures 34 formed in the frame segments 12 and 12a. As such, the connecting link 40 may span between opposite ends of the 240° ring segment 12 and 120° ring segment 12a (as represented by the phantom lines in FIG. 2), with the pair of threaded studs 42 being inserted in the endmost apertures 34 formed in the segments 12 and 12a. A pair of acorn fasteners 42 may be threadingly mounted upon the studs 42 from the reverse side of the frame segments 12 and 12a with their lower bearing surface 46 being received between the flange portions 32 of the frame segments 12 and 12a to contact the center webs portions 30.

As shown in FIG. 3, the pin holder 14 of the present invention is formed having an elongate body section 50 including a flange 51 at its distal end. The flange 51 is provided with a mounting boss 52 and threaded stud 54 which are sized to be received between the flange portions 32 of the arcuate segment 12 and within the aperture 34 of the web portion 30 respectively. The length of the boss 52 is slightly less than the distance from the outboard edge 58 of the flange portions 32 to the web 30 such that the lower surface 56 of the flange 51 may abut the outboard edges 58 of the arcuate frame segment 12.

With the threaded stud 54 of the pin holder 14 inserted through the aperture 34, an acorn fastener 60 may be threaded onto the stud 54 from the reverse side of the arcuate segment 12 thereby rigidly mounting the pin holder 14 to the frame segment. As will be recognized, by such an arrangement, the pin holder 14 may be selectively rotated about the axis of the threaded stud 54 and subsequently locked in a desired orientation by the manual tightening of the acorn fastener 60 against the web portion 30 of the arcuate segment 12.

The body section 50 of the pin holder 14 includes a plurality of apertures 62 which extend through its width, each sized to loosely receive a conventional transfixing or half pin 18 and 20 respectively. As shown in FIG. 3, the lower portion of each of the apertures 62 is, in one preferred embodiment, formed with a V-shaped wall portion 64, which feature is the invention of Charles Dohogne, having an included angle of approximately 120°.

A plurality of rectangular pockets 66 are additionally formed in the body section 50 of the pin holder 14 perpendicular to the apertures 62. The pockets 66 extend from the upper surface of the pin holder 14 and terminate at a distance below the apertures 62 but above the lower surface of the body member 50. Pockets of any other non-circular shape may, of course, be used.

Each of the pockets 66 are sized to slidingly receive a pin lock member 68 having a rectangular shaped body 70 and a threaded stud 72. The body 70 of the pin lock members 68 includes a central aperture 74 which extends through the pin lock 68 and is provided with a V-shaped wall portion 76 adjacent its upper end which is formed in the manner previously described in relation to the V-shaped wall 64 of the apertures 62. The threaded stud 72 of the pin lock 68 extends through an aperture 69, see FIG. 3A, formed centrally between the lower surface of the pocket 68 and the bottom surface of the body portion 50 of the pin holder 14.

In operation, the pin lock 68 may be loosely positioned within one of the pockets 66 formed in the body 50, and a pin 18 or 20 may be inserted through the aperture 62 formed in the body portion 50 as well as the aperture 74 formed in the pin lock 68. Subsequently, an acorn fastener 80 may be threadingly mounted onto the stud 72 causing the pin lock 68 to be pulled tightly downward against the pin 18. The pin 18 is axially centered within the pin holder 14 and is securely locked into position by the concentrated forces being exerted along the clamping lines corresponding to the contact surfaces between the outer diameter of the pin 18 with the apertures in the body and the pin lock. The "V" shaped wall portions improve the rigidity of this action.

As will be recognized, each of the pockets 66 formed in the pin holder 14 includes a pin lock member 68 which facilitate the remaining pins 18 and 20 within the aperture 62 to be securely locked into position. Additionally, by this particular arrangement, individual pins 18 or 20 may be selectively unlocked from the pin holder 14 by merely loosening the approximate acorn fastener 80 of one of the pin lock members 68. Further, the present invention contemplates the use of single, dual and triple pin receiving pin holders 14 which are formed in the manner previously described.

In FIG. 4, the detailed construction of the adjustable rod 16 of the present invention is illustrated. The rod 16 comprises an inner and outer tube member 90 and 92 which are adapted for relative telescoping movement. The outer tube 92 includes an elongate slot 94 which extends substantially throughout its length. The inner tube 90 is formed having an inner aperture 96 which terminates adjacent its distal end and includes a threaded aperture 98 positioned perpendicular to its axis.

The inner and outer tubes 90 and 92 are assembled together by a threaded fastener 100 which cooperates with a saddle 102 and extends through the slot 94 and into the aperture 98. By manually tightening the threaded fastener 100, the saddle 102 engages the outer diameter of the outer tube 92 and positively locks the inner tube 90 at any location along the length of the slot 94.

The opposite end of the inner tube 90 includes a knurled knob 104 which is mounted thereby by means to permit rotation of the knob 104 about the tube 90 while maintaining the axial position of the knob 104 at the end of the tube 90. The knob 104 is provided with a threaded central aperture 106 which threadingly engages a lead screw 108. The diameter of the aperture 96 of the inner tube 90 is sized to be slightly greater than the maximum diameter of the lead screw 108 such that manual turning of the knob 104 causes the lead screw 108 to freely reciprocate axially within the aperture 96 of the tube 90.

The distal ends of the outer tube 94 and lead screw 108 are each rigidly attached to a clevis 110 formed in a conventional manner. The clevis 110 mounts a trunion 112 as by way of a threaded trunion pivot 114 and fastener 116. The trunions 112 additionally mount a similarly formed clevis 118 having a trunion pivot 120 and fastener 122 cooperating therewith. The distal ends of the clevis 118 are provided with a mounting flange 124 and threaded stud 126 which permit the entire adjustment rod assembly 16 to be secured to the pair of arcuate frame segments 12 in a manner previously described in relation to the pin holder 14 mounting.

By this particular arrangement, it will be recognized that connecting rod 16 may be loosely attached to the arcuate frame segments 12 with the trunion clevis assemblies at opposite ends of the rod 16 forming universal joints to permit angular and lateral articulation of the frame segments 12. Additionally, the length of the adjustment rod 16 may be varied first by a fast adjustment provided by the reciprocation of the inner tube 90 within the outer tube 92, and secondly by the fine adjustment provided by the reciprocation of the lead screw 108 within the inner tube 90. Once the correct positioning of the adjustment rod 16 is obtained, the entire assembly may be rigidly locked into position by the manual tightening of the threaded fasteners 122, 116, 100 and 60. An additional locking nut is provided on lead screw 108 in practice but is omitted on the drawing for clarity of illustration.

Referring to FIG. 5, sheath 130 is specifically designed for use with the pin holder 14 during installation of the device 10 upon the patient. The sheath 130 comprises an elongate tubular member 132, having an inside diameter slightly greater than the diameter of the transfixing and half pins 18 and 20 respectively, and an outside diameter slightly less than the diameter of the apertures 62 and 74 formed in the pin holder 14 and pin lock member 68 respectively.

One end of the sheath 130 includes a pair of mounting collars 134 and 136 which are preferably press fit onto the end of the sheath 130 and mount a tab 138 which extends radially outward to form a handle for the sheath 130. The opposite end of the tube member 132 is formed having a sharpened toothlike edge 140 which is adapted to anchor itself into the cortices of the bone. The use of the sheath 130 in combination with the pin holder 14 of the present invention, provides an alignment process for the drilling and placement of pins through the bone 13, and prevents excessive damage to the soft tissue surrounding the bone.

A bone depth gauge 150 which is preferably utilized in combination with the sheath 130 is depicted in FIG. 7. The depth gauge 150 comprises a tubular handle member 152 which slidingly mounts an elongate probe 174. The probe 174 is sized to be substantially greater in length than the sheath 130 and has a maximum diameter slightly less than the inside diameter of the sheath 130. The lowermost end of the probe 174 is provided with a reduced diameter section 176 which terminates at its lowermost end in a tapered shank 178. A blunt buttonlike end member 180 is mounted to the lower end of the tapered shank 178 having an upper surface 182 which forms a shoulder substantially perpendicular to the axis of the probe 174.

The opposite end of the probe 174 is provided with an indicator tab 184 which is attached to the probe 174 by a pair of wire mounts 186 sized to reciprocate through the slot 188 formed in the handle member 152. The indicator tab 186 is adapted to be gripped by the physician, wherein movement of the tab 186 causes the probe 174 to reciprocate axially throughout the length of the handle member 152. The handle member 152 is additionally provided with a series of graduations along its outer diameter 190 which may be utilized in conjunction with the tab indicator 184 to determine the bone diameter.

For purposes of illustration, the apparatus 10 will be described in relation to a typical long bone fracture 15 as depicted in FIG. 1, however, the same installation and operation are applicable to other bone fractures as well.

After the extent and location of the bone fracture 15 have been determined, the proper diameter size and angular length of the arcuate frame segments 12 to be utilized upon the patient must be selected. Typically, the diameter size is selected to position the segments 12 as close as possible to the soft tissue of the patient while providing for usual swelling during healing. The angular length of the segments 12 are determined by the particular types of bone fracture.

A small incision is made in the soft tissue at a location spaced on one side of the fracture site, and a hole of proper size to receive a transfixing pin 18 is drilled entirely through the bone 13 preferably oriented perpendicular to the bone 13. A first transfixing pin 18 may then be inserted through the incision and threaded into the cortices of the bone 13 having opposite ends of the transfixing pin 18 extending outward a short distance beyond the soft tissue surrounding the bone 13.

With the first transfixing pin 18 positioned within the bone 13, a pair of pin holders 14 may be mounted onto the opposite ends of the transfixing pin 18 which extend outboard of the soft tissue and preliminarily maintained in place by the finger tightening of the appropriate acorn fasteners 80 of the pin holders 14. The pair of pin holders 14 are then attached to one of the arcuate frame segments 12 (e.g., the proximal frame segment) at positions approximately 90° from the center of the frame segment 12. Minor movement of the pin holder 14 along the length of the transfixing pin 18 to permit insertion of the threaded studs 54 into the segment apertures 34 may be accommodated by slightly loosening the acorn fastener 80 and the pin holders 14 may be secured to the frame 12 by manual tightening of the similar acorn fasteners 60 onto the rear side of the frame 12. During this initial mounting procedure, the arcuate support segment 12 should be substantially centered about the soft tissue of the extremity, and disposed in a plane substantially perpendicular to the bone 13.

Once the frame 12 has been preliminarily mounted to the transfixing pin 18 by way of the pin holders 14, two additional transfixing pins 18 may be inserted through the bone 13 and attached to the pin holders 14. The preferred procedure for facilitating the placement of these additional transfixing pins 18 is illustrated schematically in FIGS. 6, 8, 10 and 11 wherein the pin holder 14 attached to the frame segment 12 is utilized in conjunction with the sheath 130 to accurately align and position the pin 18 through the bone 13.

The first step in this procedure is the insertion and preliminary locking of the tubular portion 132 of the sheath 130 into the adjacent aperture 62 formed in the pin holder 14. An incision is made where the lower end 140 of the sheath 130 contacts the soft tissue and, the sheath 130 is pressed through the soft tissue to contact the bone 13. The uppermost collar 136 of the sheath 130 may then be moderately tapped downward with a mallet 13', causing the knife edge end 140 of the sheath to attach itself to the bone 13. The outer diameter 132 of the sheath 130 is registered within the aperture 62 of the pin holder 14 thereby maintaining sheath 130 in a parallel orientation to the first transfixing pin 18 locked within the pin holder 14.

With the sheath 130 in place, a drill 200 may be inserted through the open end of the sheath 130 and a hole formed through the bone 13 (as shown in FIG. 8). As will be recognized, during this drilling procedure, the sheath 130 acts as a drill guide to prevent wandering of the drill through the bone 13. Subsequently, the drill 200 may be removed from the sheath 130 and the transfixing pin 18 may be inserted therein (as shown in FIG. 10) and threaded through the bone 13. The acorn fastener 80 holding the sheath 130 in the pin holder 14 may be manually loosened and the sheath 130 may be withdrawn from the soft tissue (as shown in FIG. 11) and removed from the pin holder 14 leaving the transfixing pin 18 in place. The acorn fastener 80 may then be retightened thereby securely clamping the transfixing pin 18 in place. This above procedure may be repeated for the third transfixing pin 18 in the assembly such that three parallel transfixing pins 18 extend through the bone 13 and are affixed to the proximal arcuate frame segment 12 by the pair of pin holders 14.

With the three parallel transfixing pins mounted to the bone 13, an additional pair of half pins 20 may be inserted through the bone 13 extending in a plane substantially perpendicular to the plane of the previously positioned transfixing pins 18. The insertion of the half pins is accomplished in a manner similar to the transfixing pins 14; however, a dual pin holder 14 is utilized in place of the triple pin holder 14 previously described. As shown in FIG. 1, the dual pin holder 14 is positioned at the approximate center line of the proximal arcuate frame segment 12 preferably located at no more than a 30° angle therefrom. The dual pin holder 14 is formed in the same manner as the triple pin holder 14 (shown in FIG. 3) except that the center line of the pin receiving apertures 62 are offset to facilitate the half pins 20 entering the bone 13 at a location between the transfixing pins 18.

As with the insertion of the previous transfixing pins 18, the sheath 130 is inserted into the aperture 62 formed in the dual pin holder 14 and an incision is made in the soft tissue beneath the end of the sheath 130. The sheath 130 is subsequently inserted through the soft tissue and lodged in the bone 13. The drilling of the hole through the bone 13 may then be accomplished using the sheath 130 as a drill guide.

The half pins 20 extend through the soft tissue only on one side of the bone 13 and must be accurately positioned within the bone 13 to contact both cortices 202 (shown in FIG. 6) while extending only a minimum distance below the lower surface of the bone. As such, prior to the insertion of the half pins, it is necessary to accurately determine the bone diameter. In the preferred embodiment this diameter determination is readily facilitated by use of a bone depth gauge 150 of FIG. 7.

As previously mentioned, the probe 174 of the depth gauge 150 is sized to be inserted within the sheath 130 (as shown in FIG. 9). By gripping the handle portion 152 of the depth gauge 150, the surgeon may lower the probe end 176 of the depth gauge 150 downward through the sheath 130 to contact the blunt button-like 180 upon the top surface of the bone (as shown in FIG. 12). Upon contact therewith, the surgeon may visually inspect one end of the indicator tab 184 to obtain an initial reading (as shown in FIG. 12) on the graduated scale 190. Subsequently, the probe end 176 of the depth gauge 150 may be reciprocated through the previously drilled hole in the bone, by manual sliding of the indicator tab relative the handle 152 until the shoulder 182 of the probe end 180 hooks the lower outside surface of a bone 13 (as shown in FIG. 13). The indicator tab 184 may then be visually inspected again, to obtain a new reading (as shown in FIG. 13) and the difference in the two readings on the graduated scale 190 will represent the outside diameter of bone 13.

The depth gauge 150 may then be removed from the sheath 130 and the proper size half pin 20 lowered through the sheath 130 and inserted into the bone 13. The bone diameter having been determined by the depth gauge 150, the half pin threadingly engages both cortices 202 of the bone and is made to protrude only a short distance beyond the bone 13 to eliminate damage of muscle tissue on the undersurface of the bone or the rupturing of an artery. The sheath 130 may then be removed from the pin holder 14, and the acorn fastener 80 retightened to securely mount the pin to the pin holder 14. Similarly, the second half pin may be inserted into the bone 13 in the same manner and locked in position upon the pin holder 14.

By such a procedure, it will be recognized that the bone 13 is positively located from two substantially perpendicular directions, or at other selected angles, to the proximal arcuate support segment 12 with the support segment 12 providing a rigid structure which prevents movement of the proximal end of the bone 13 relative the support frame 12. Additionally, it will be recognized that by use of the sheath 130 during the installation process, the pin holes may be drilled and accurately located with only minimal disturbance of the soft tissues surrounding the bone 13 thereby preventing any unnecessary damage to the soft tissue.

The above procedures may be repeated for the distal end of the bone 13 whereby a second series of transfixing pins 18 and half pins 20 are rigidly attached to the bone 13 as well as the distal arcuate frame segment 12. As such, both the proximal and distal ends of the bone 13 are rigidly affixed to a respective arcuate frame segment 12.

Subsequently, three adjustment rods 16 may be loosely attached to extend between the pair of arcuate frame segments 12 by inserting the threaded studs 126 located on opposite ends of the rods through a respective aperture 34 formed in the frame segments 12 and loosely tightening the respective acorn fasteners 60 (FIG. 4) onto the frame section 12. During the initial connection, the screw fastener 100 upon the saddle 102 is loosened to provide free reciprocation of the inner tube 90 within the outer tube 94 of the connecting rod 16 and the knurled knob 104 is preliminarily positioned midway along the length of the lead screw 108. Additionally, the clevis and trunion assembly nuts 116 and 122 are loosened to provide universal articulation of the rod 16 at its opposite ends.

The fracture 15 may then be set by grasping both of the arcuate frame segments 12 and moving the same relative to one another until proper alignment of the bone ends in the vicinity of the fracture 15 is obtained. The screw fasteners 100 may then be securely tightened thereby locking the inner tubes 90 in position within the outer tubes 92 of the connecting rods 16 and the clevis trunion assembly nuts 122 and 116 tightened to prevent pivotal movement of the assembly. The knurled knobs 104 of each of the adjustable rods 16 may then be manually turned causing their respective lead screws 108 to be reciprocated either inward or outward within the inner tube 90 to apply distraction or compression to the bone fracture 15. Subsequently, all of the acorn fasteners may be tightly set by use of a conventional wrench to maintain the set configuration of the external fixation device 10.

As will be recognized, by such an installation, the bone 13 is completely immobilized with the majority of the compression, tensile and bending forces applied during bone positioning being carried by the arcuate frame segments 12. Additionally, due to the frame segments 12 extending proximal to the soft tissue of the patient, patient discomfort is minimized and access to the soft tissue in the vicinity of the fracture 15 is readily facilitated. Thus, needed procedures such as grafting and irrigation may be readily accomplished without interference of the apparatus 10. Further, due to the unique pin holder 14 design of the present invention which permits independent locking of the pins 18 and 20, selected pins 18 or 20 may be repositioned or removed during postoperative care without disturbing the remaining pins on the apparatus.

Those skilled in the art will recognize that the apparatus 10 of the present invention may be readily modified with varying pin locations, and number of frame segments and adjustment rods utilized to facilitate the proper external fixation for the particular bone fracture, and such modifications are encompassed within the scope of the present invention.

I claim:

1. A method of installing a pin extending from the soft tissue and bone of a user substantially parallel with a previously installed pin in an external fixation device comprising the steps of:

clamping an exposed free end of said previously installed pin into one aperture of a multi-aperture pin holder;

inserting a tubular sheath through an adjacent one of said apertures in said pin holder;

extending said sheath through said soft tissue to contact said bone;

inserting a drill through said sheath to drill a hole through said bone along an axis parallel to the axis of said sheath;

removing said drill from said sheath;

measuring the diameter of said bone at the location of said hole;

inserting a pin through said sheath and into said hole drilled in said bone;

withdrawing said sheath from said pin holder while maintaining said pin within said bone; and clamping the exposed free end of the newly installed pin into said adjacent aperture in said pin holder.

2. The method of claim 1 wherein said sheath insertion step comprises the further step of striking said sheath to anchor said sheath into the cortices of said bone.

3. The method of claim 1 wherein said measuring step comprises the steps of:

inserting a depth gauge having a calibrated handle portion, a probe portion, and an indicator tab attached to said probe portion and reciprocable along the length of said handle portion, through said sheath to contact the end of said probe portion against the proximal surface of said bone;

visually inspecting the axial position of said indicator tab along the length of said calibrated handle to obtain an initial depth reading;

lowering said probe portion through said drilled hole in said bone to contact the distal surface of said bone by reciprocating said indicator tab along the length of said calibrated handle portion;

visually inspecting the axial position of said indicator tab along the length of said calibrated handle portion to obtain a final depth reading; and calculating the difference between said initial and final depth readings, said difference representing the diameter of said bone.

4. The method of claim 1 wherein said previously installed pin passes from said pin holder through the bone to a second pin holder on the opposite side of the bone, the method further comprising passing the pin being installed through the bone into said second pin holder and clamping the pin therein.

5. The method of claim 1 wherein after inserting said sheath into said aperture and before inserting said drill in said sheath, said sheath is clamped in said holder by clamping means in said holder.

* * * * *